(12) United States Patent
Kaintz et al.

(10) Patent No.: US 12,329,951 B2
(45) Date of Patent: Jun. 17, 2025

(54) CARTRIDGE LOADING SYSTEM FOR SYRINGE CAPS

(71) Applicant: Omnicell, Inc., Mountain View, CA (US)

(72) Inventors: Ryan Kaintz, Allison Park, PA (US); Peter Hoffman, Seattle, WA (US)

(73) Assignee: Omnicell, Inc., Cranberry Township, PA (US)

( * ) Notice: Subject to any disclaimer, the term of this patent is extended or adjusted under 35 U.S.C. 154(b) by 0 days.

(21) Appl. No.: 18/637,518

(22) Filed: Apr. 17, 2024

(65) Prior Publication Data

US 2024/0261513 A1 Aug. 8, 2024

Related U.S. Application Data

(62) Division of application No. 17/005,650, filed on Aug. 28, 2020, now Pat. No. 11,980,748.

(51) Int. Cl.
*A61M 5/32* (2006.01)
*A61M 5/31* (2006.01)

(52) U.S. Cl.
CPC ... *A61M 5/3202* (2013.01); *A61M 2005/3104* (2013.01); *A61M 2207/10* (2013.01); *Y10T 29/53339* (2015.01)

(58) Field of Classification Search
CPC ........ A61M 5/3202; A61M 2005/3104; A61M 2207/10; Y10T 29/53339; B65B 3/003; B65B 7/28; B65B 7/2807; B65B 7/2835; B65B 43/60; B65B 57/02; G01N 2021/845; G01N 21/90
See application file for complete search history.

(56) References Cited

U.S. PATENT DOCUMENTS

| 3,128,911 | A | 4/1964 | Morris et al. |
| 5,699,654 | A | 12/1997 | Van Den Akker |
| 6,991,002 | B2 * | 1/2006 | Osborne ................. B65B 3/003 604/416 |
| 10,806,676 | B2 * | 10/2020 | Fisher ..................... G16H 20/13 |
| 11,980,748 | B2 | 5/2024 | Kaintz et al. |
| 2002/0020459 | A1 * | 2/2002 | Baldwin ................. B65B 3/006 141/11 |
| 2004/0050991 | A1 | 3/2004 | Hiraguchi |
| 2006/0259195 | A1 * | 11/2006 | Eliuk .................. B01F 33/8442 700/245 |

(Continued)

OTHER PUBLICATIONS

Supplemental Search Report for European Patent Application No. 21862434.3, mailed Oct. 16, 2024, 8 pages. European Patent Office, Munich, Germany.

(Continued)

*Primary Examiner* — Lee A Holly
(74) *Attorney, Agent, or Firm* — Kilpatrick Townsend & Stockton LLP; Darin J. Gibby; Torrey D. Spink

(57) ABSTRACT

A cartridge and loading system for loading tamper-evident syringe caps into a robotic pharmaceutical compounding device. The compounding device has a syringe finishing station, and can transfer tamper-evident caps from the cartridge to the syringe finishing station. The cartridge has a floor disposed at an angle to horizontal. The device may include a vibratory element for vibrating the cartridge, so that tamper-evident caps are fed to an outlet of the cartridge by gravity.

18 Claims, 12 Drawing Sheets

(56) References Cited

U.S. PATENT DOCUMENTS

| | | |
|---|---|---|
| 2012/0241043 A1 | 9/2012 | Perazzo et al. |
| 2013/0145725 A1 | 6/2013 | Bianco |
| 2016/0176550 A1 | 6/2016 | Viitello et al. |
| 2018/0037343 A1 | 2/2018 | Procyshyn et al. |
| 2018/0105294 A1 | 4/2018 | Abboud et al. |

OTHER PUBLICATIONS

U.S. Appl. No. 17/005,650 , Advisory Action, Mailed on Nov. 24, 2023, 6 pages.
U.S. Appl. No. 17/005,650 , Final Office Action, Mailed on Sep. 13, 2023, 16 pages.
U.S. Appl. No. 17/005,650 , Non-Final Office Action, Mailed on Mar. 14, 2023, 12 pages.
U.S. Appl. No. 17/005,650 , Notice of Allowance, Mailed on Jan. 10, 2024, 12 pages.
Application No. PCT/US2021/046884 , International Preliminary Report on Patentability, Mailed on Mar. 9, 2023, 9 pages.
Application No. PCT/US2021/046884 , International Search Report and Written Opinion, Mailed on Nov. 26, 2021, 10 pages.

\* cited by examiner

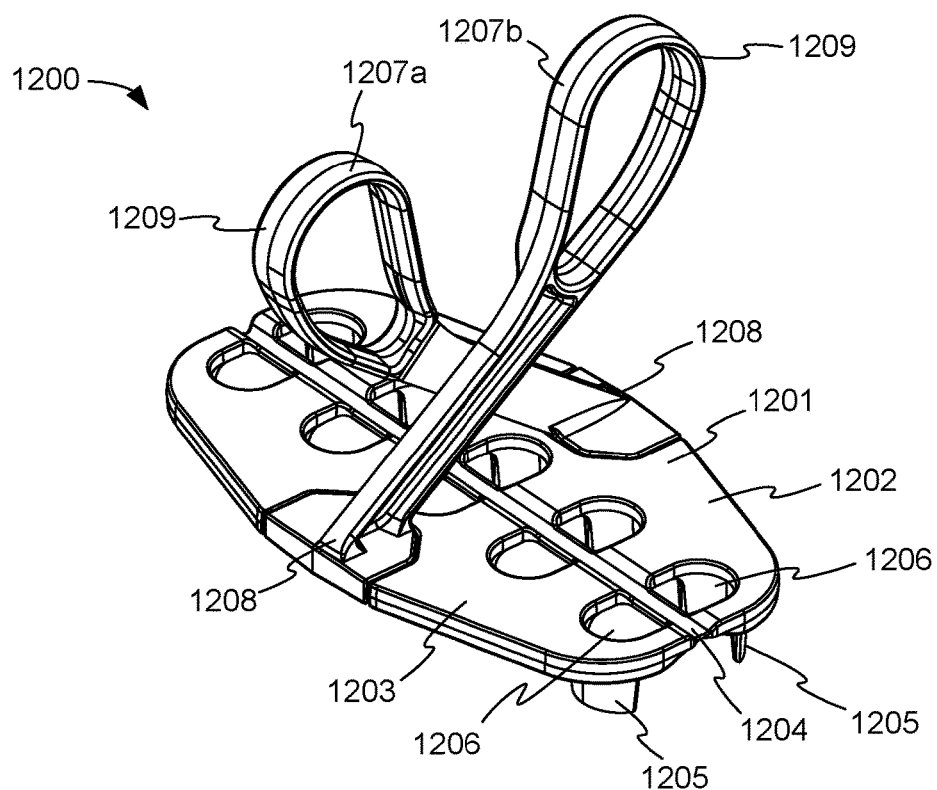
FIG. 12
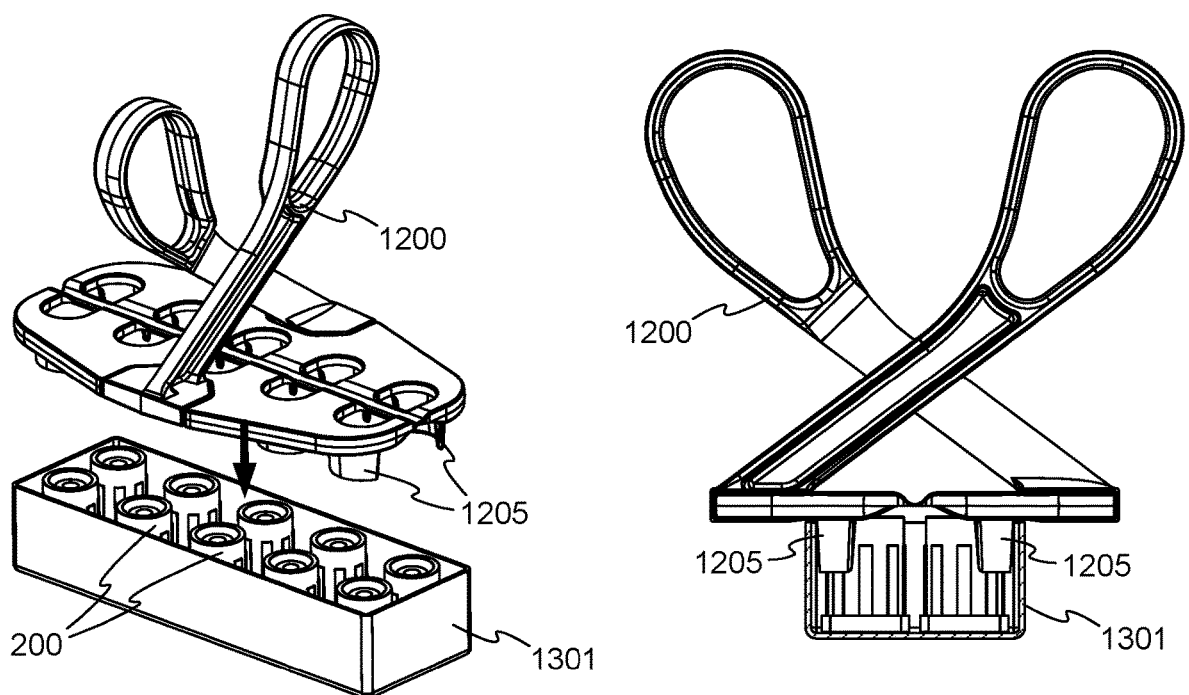
FIG. 13
FIG. 14

CARTRIDGE LOADING SYSTEM FOR SYRINGE CAPS

CROSS REFERENCES TO RELATED APPLICATIONS

This application is a divisional of U.S. Non-Provisional patent application Ser. No. 17/005,650, filed Aug. 28, 2020, titled "CARTRIDGE LOADING SYSTEM FOR SYRINGE CAPS", which is related to U.S. patent application Ser. No. 17/005,786, filed concurrently herewith and titled "MEDICATION DOSING SYSTEMS AND METHODS"; U.S. patent application Ser. No. 17/005,637, filed concurrently herewith and titled "BAG TRANSFER MECHANISM FOR IV COMPOUNDING"; U.S. patent application Ser. No. 17/006,027, filed concurrently herewith and titled "SYSTEMS AND METHODS FOR PARALLEL PREPARATION PROCESSING"; and U.S. patent application Ser. No. 17/005,803, filed concurrently herewith and titled "CABINET WITH INTEGRATED PICK-AND-PLACE MECHANISM"; the disclosures of which are hereby incorporated by reference herein in their entireties for all purposes.

BACKGROUND OF THE INVENTION

Pharmaceutical compounding is the preparation of patient-specific medications by the processing or combination of ingredients. Many medications, especially medications administered orally in pill form, are now manufactured in a variety of forms and dosages so that little preparation is needed at a pharmacy, other than placing the proper number of pills in a bottle to fill a doctor's prescription for a particular patient. However, medications for administration by injection are routinely compounded, for example in hospital pharmacies, especially for expensive or hazardous drugs.

Typically, a physician will prescribe a particular medication in a specific dose for a specific patient, for administration by injection. The pharmacy receives the prescription and fills a syringe with the proper amount of the medication. The filled syringe is then sent to the hospital floor for administration to the patient.

Much of the work of compounding may be performed by robotic compounding machines. The variety of materials that must be handled by the robotic machines may present challenges. For example, the machine may automatically draw medication into the syringe from a vial and remove the needle from the syringe before delivering the filled syringe. It is very important that the compounding be performed without the introduction of contaminants. For example, the completed syringe should be capped with a sterile, tamper-evident cap before delivery from the compounding machine.

There is a need for improved systems and methods for preparing medications for administration by injection.

BRIEF SUMMARY OF THE INVENTION

According to one aspect, a robotic compounding system comprises a syringe finishing station having an input location configured to individually receive tamper-evident syringe caps and to individually place the tamper-evident syringe caps onto syringes, and a cartridge that is configured to hold a supply of tamper-evident syringe caps. The cartridge has an outlet positioned adjacent the input location of the syringe finishing station, and the cartridge comprises a floor that is angled toward the outlet to facilitate movement of the tamper-evident syringe caps toward the outlet. In some embodiments, the syringe finishing station is configured to rotate a tamper-evident cap about a horizontal axis in order to place the tamper-evident cap on a syringe. In some embodiments, the robotic compounding system further comprises a vibratory element configured to vibrate the cartridge, to cause the tamper-evident caps to travel by virtue of gravity toward the outlet of the cartridge. In some embodiments, each of the tamper-evident caps has an open end and a closed end, and the tamper-evident caps are held in the cartridge with their closed ends on the floor of the cartridge. In some embodiments, the cartridge further comprises a door that automatically closes when the cartridge is removed from the robotic compounding system. In some embodiments, the syringe finishing station comprises a feature that opens the door when the cartridge is inserted into the robotic compounding system. In some embodiments, the robotic compounding system further comprises a set of rails into which the cartridge slides to bring the outlet of the cartridge to the input location of the syringe finishing station. In some embodiments, the syringe finishing station further comprises a gate at the input location, and an actuator configured to open the gate to selective admit a tamper-evident cap from the outlet of the cartridge into the input location of the syringe finishing station. In some embodiments, the gate is closed after each dispensing of a tamper-evident cap from the cartridge.

According to another aspect, a cartridge for holding tamper-evident syringe caps comprises a flat floor and opposing side walls rising from the floor. The floor and side walls define a storage volume, and the side walls include curved sections that approach each other such that the storage volume narrows toward an outlet of the cartridge. The cartridge further comprises an end wall opposite the outlet of the cartridge, a cover that snaps onto the side walls to enclose the storage volume, and a spring-loaded door that by default closes off the outlet of the cartridge. In some embodiments, the cartridge further comprises a supply of tamper-evident syringe caps contained in the cartridge. In some embodiments, the cartridge further comprises a hook adjacent the outlet, for removably retaining the cartridge in a compounding system. In some embodiments, the cover can be disengaged from the rest of the cartridge without the use of tools.

According to another aspect, a method of loading tamper-evident syringe caps into a robotic compounding device comprises providing a cartridge having a storage volume for containing the tamper-evident syringe caps, placing a supply of tamper-evident syringe caps into the cartridge, and inserting the cartridge into the robotic compounding device. In some embodiments, the cartridge comprises a flat floor; opposing side walls rising from the floor, the floor and side walls defining the storage volume, and the side walls including curved sections that approach each other such that the storage volume narrows toward an outlet of the cartridge; an end wall opposite the outlet of the cartridge; a cover that snaps onto the side walls to enclose the storage volume; and a spring-loaded door that by default closes off the outlet of the cartridge. In some embodiments, the method further comprises vibrating the cartridge to cause tamper-evident caps to travel under the influence of gravity toward an outlet of the cartridge.

According to another aspect, a tool for bulk loading of tamper-evident syringe caps into a cartridge comprises a main body having two portions joined by a hinge, and two rows of gripping features descending from the main body, one row of gripping features on each side of the hinge. The tool further comprises two crossed levers, each of the levers having a proximal end and a distal end, the proximal ends of the two levers joined respectively to opposite edges of the main body. The main body and the two levers are configured such that bringing the distal ends of the two levers closer together bends the main body at the hinge, and brings the two rows of gripping features closer together. In some embodiments, the main body is monolithic, and the hinge is a living hinge. In some embodiments, the main body defines two rows of openings through the main body, one opening respectively for each of the gripping features.

BRIEF DESCRIPTION OF THE DRAWINGS

FIG. 12 illustrates a tool for efficient filling of a cartridge with tamper-evident caps, in accordance with embodiments of the invention.

FIG. 13 shows the tool of FIG. 12 poised to engage with package of tamper-evident caps.

FIG. 14 is a cross section view of tool the tool of FIG. 12 and the package of FIG. 13, after engagement.

DETAILED DESCRIPTION OF THE INVENTION

In previous robotic compounding devices, tamper-evident caps have been inserted manually into the robot compounding devices, one at a time by an operator. This technique is time consuming, operator-intensive, and presents challenges for the prevention of contamination. For example, the caps may be handled in open air outside the sterile interior of the robotic compounding device.

In embodiments of the invention, a number of tamper-evident caps are loaded into a cartridge, which is then inserted into the robotic compounding device. The caps are automatically fed to a syringe finishing station, for attachment to filled syringes. The cartridge may be filled in a sterile environment, for example under a hood flowing filtered air over the cartridge, facilitating maintenance of sterility of the caps. The various parts of the cartridge may be cleaned or sterilized before loading, and the cartridge may be wiped down again after loading.

Because the caps are loaded in bulk into the cartridge, operator time is used much more efficiently. And because the caps are enclosed within the cartridge, they are much less susceptible to contamination than in previous systems.

Figure 1:
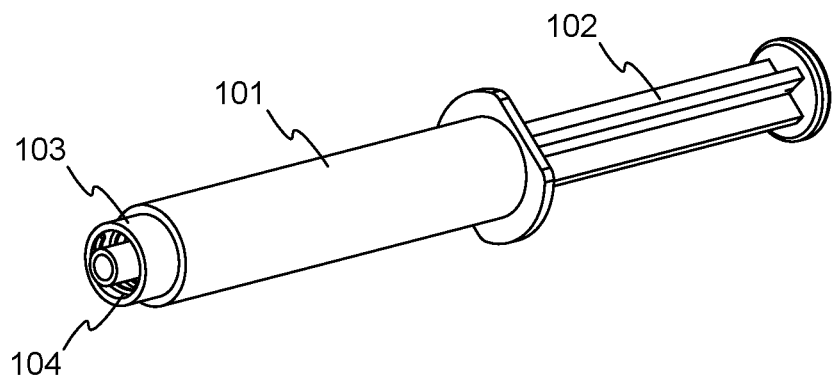
FIG. 1 illustrates a simplified sketch of a typical syringe.

FIG. 1 illustrates a simplified sketch of a typical syringe 100. Syringe 100 includes a barrel 101 for holding liquid, a plunger 102 for drawing liquid into barrel 101 and injecting liquid out of barrel 101, and a standard luer connector 103 for attaching a needle, injection tubing, or other items. Luer connector 103 includes internal threads 104, for facilitating such connections.

Figure 2:
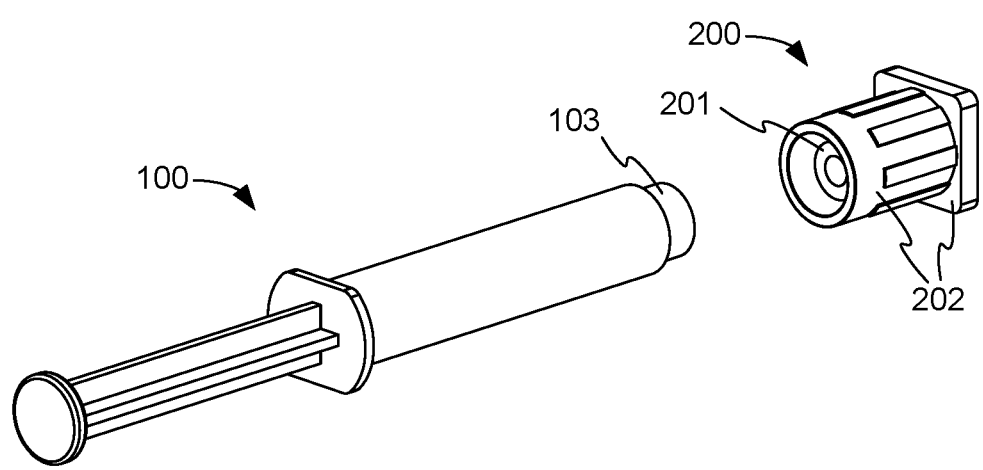
FIG. 2 illustrates the syringe of FIG. 1 with a tamper-evident cap.

FIG. 2 illustrates syringe 100 with a tamper-evident cap 200. In this example, inner portion 201 of tamper evident cap 200 is configured to engage the threads 104 of luer connector 103 of syringe 100. Outer portion 202 engages with inner portion 201 such that when outer portion 202 is turned in a "right hand" direction, inner portion 201 is driven into connection with luer connector 103. However, when outer portion 202 is turned in a "left hand" direction, it turns freely, and cannot be used to withdraw inner portion 201 from luer connector 103. To remove tamper-evident cap 200 from syringe 100, it is necessary to pull outer portion 202 axially off of inner portion, and then remove inner portion by unthreading it from luer connector 103. The act of removing outer portion 202 axially breaks an indicator component of tamper-evident cap 200, and thus illicit tampering with filled syringe 100 may be detected. In this example, tamper-evident cap 200 is a model TEC-1000 cap available from B. Braun Medical Inc., of Bethlehem, Pennsylvania, USA. However, other embodiments of the invention may use other kinds of tamper-evident caps, having different mechanisms for indicating possible tampering.

Figure 3:
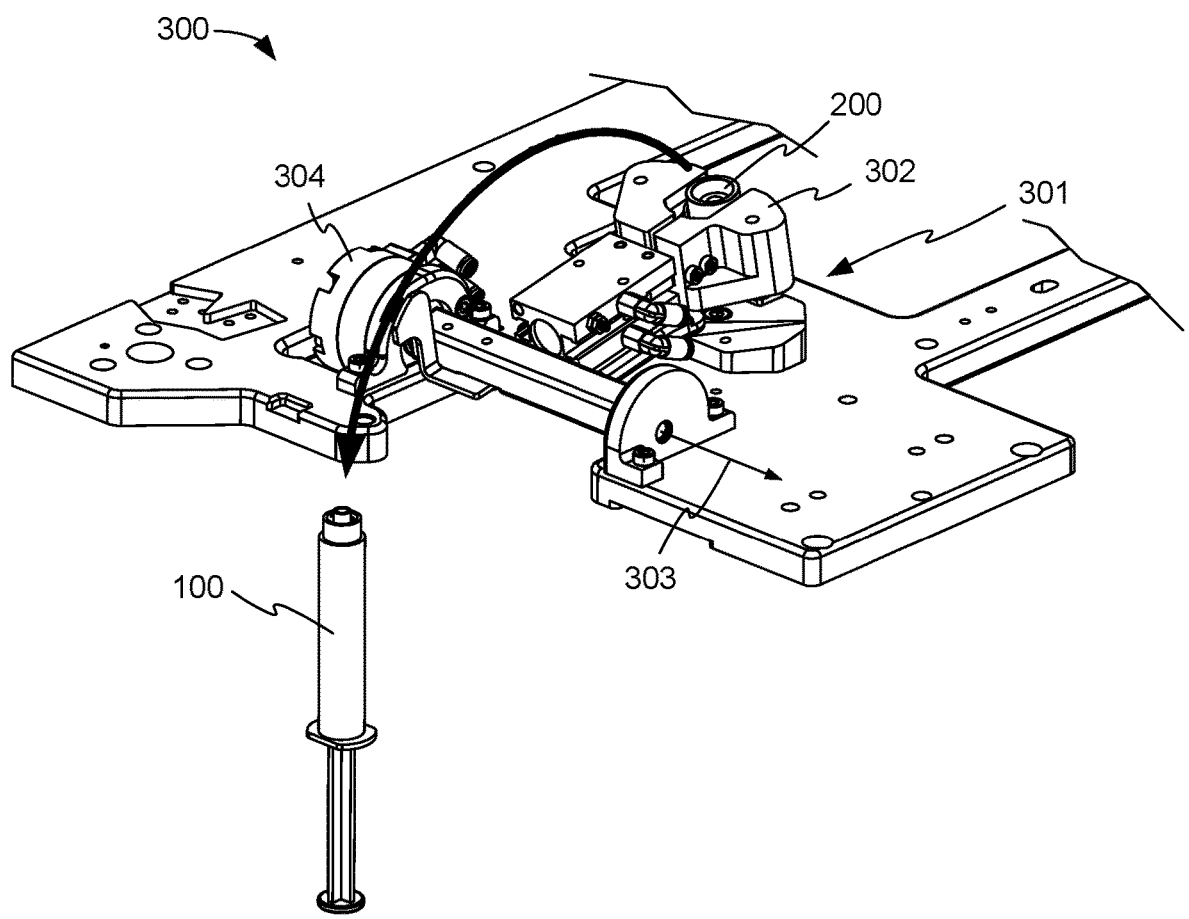
FIG. 3 illustrates a portion of a syringe finishing station of a robotic compounding device, in accordance with embodiments of the invention.

FIG. 3 illustrates a portion of a syringe finishing station 300 of a robotic compounding device, in accordance with embodiments of the invention. The vast majority of the robotic compounding device is omitted from FIG. 3, as well as much of syringe finishing station 300, in order that the most pertinent features may be clearly illustrated. For example, in this and other figures, electrical wiring, pneumatic hoses, and the like are omitted for clarity.

In FIG. 3, syringe 100 has been filled with a prescribed amount of liquid, and is ready to be "finished". Finishing station 300 may remove any needle that may have been used in filling syringe 100, may apply a label to syringe 100, and in particular adds a tamper-evident cap 200 to syringe 100. Syringe 100 is held in position by another portion of the robotic compounding device, for example a robotic arm or other mechanism, not shown. A tamper-evident cap 200 is staged in a capping mechanism 301. Capping mechanism 301 includes a gripper 302 configured to rotate about an axis 303 to bring tamper-evident cap 200 into engagement with syringe 100. Rotation of gripper 302 may be actuated in any suitable way, for example using a pneumatic actuator 304, or a suitable motor.

Figure 4:
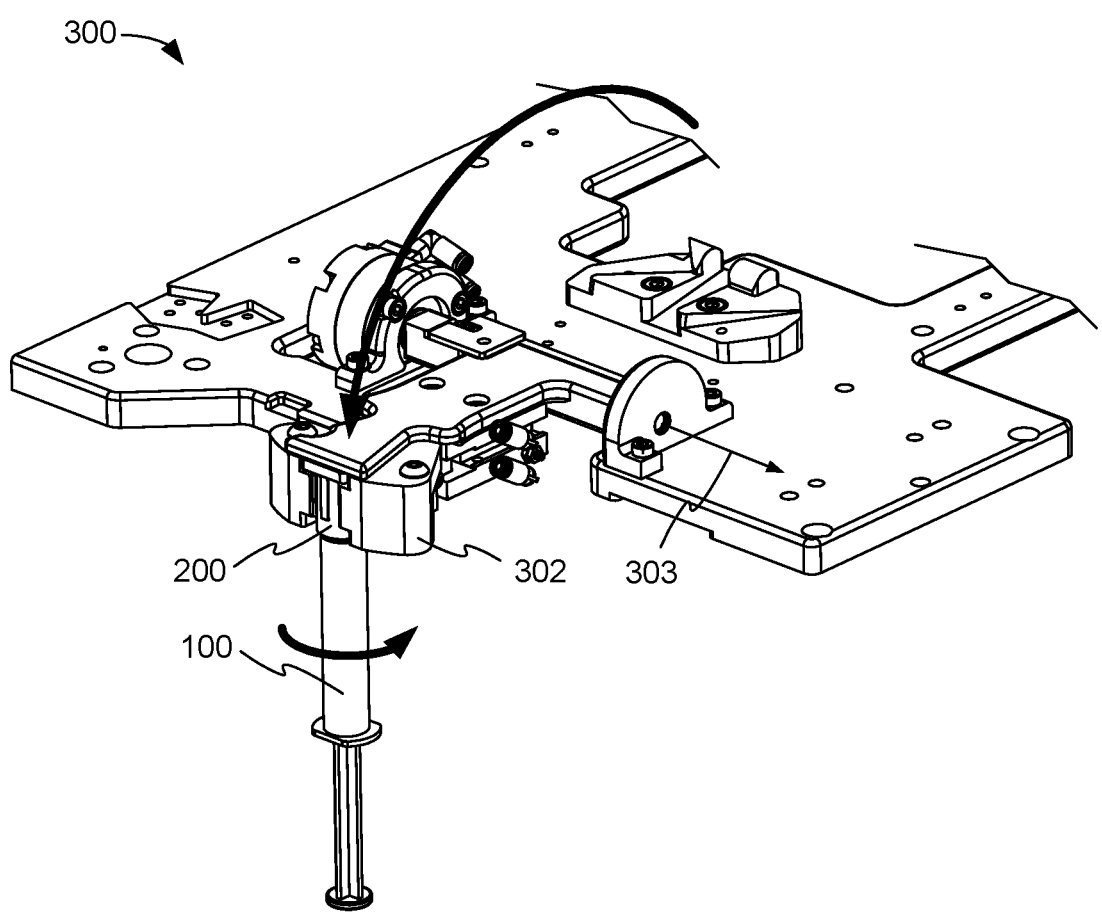
FIG. 4 shows the syringe finishing station of FIG. 3 after rotation of a gripper.

FIG. 4 shows syringe finishing station 300 after rotation of gripper 302. Tamper-evident cap 200 is brought into alignment with syringe 100, and may be secured to syringe 100 by rotating syringe 100 as shown to thread tamper-evident cap 200 onto syringe 100. In other embodiments, tamper evident cap 200 may be rotated to make the connection.

During handling of syringe 100, including filling and finishing, syringe 100 may be held in a vertical orientation, with luer connector 103 upward. This orientation may facilitate cleanliness of syringe 100. Luer connector 103 may be considered a "critical site" for which cleanliness is especially important. Holding syringe 100 in the vertical orientation shown in FIGS. 3 and 4 may present "first air" to luer connector 103 for as much of the time as possible. The term "first air" refers to air that flows from a filter and does not encounter any other item before washing over syringe 100. As such, first air has not had any chance to take up particles or other contaminants from other items inside the robotic compounding device before washing over luer connector 103.

Figure 5:
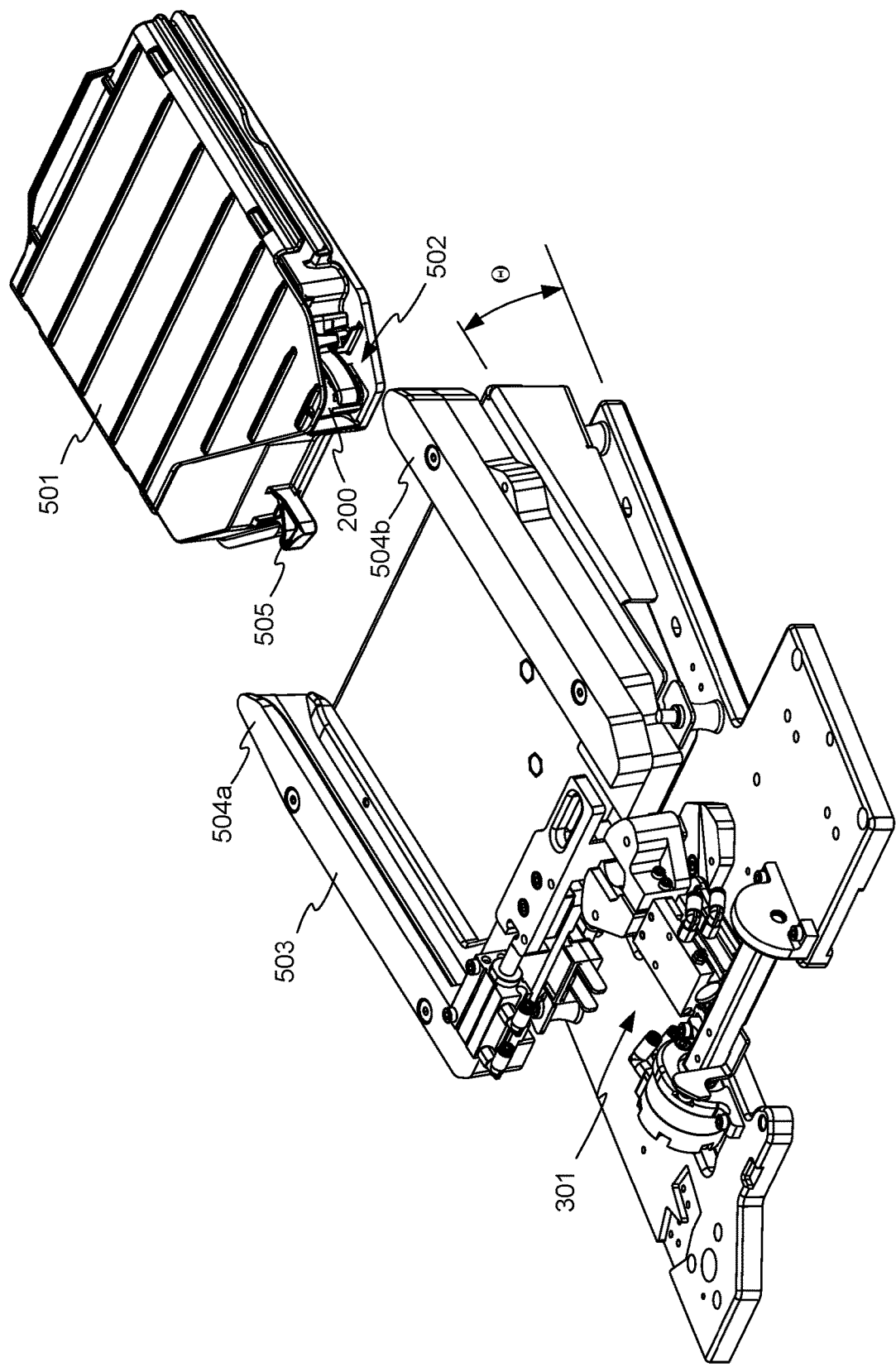
FIG. 5 shows an upper oblique view of a portion of a robotic compounding device, in accordance with embodiments of the invention.

FIG. 5 illustrates an upper oblique view of a portion of a robotic compounding device, in accordance with embodiments of the invention. A cartridge 501 is configured to hold a supply of tamper evident caps 200, one of which is visible at an outlet 502 of cartridge 501. A vibratory cradle 503 includes two channels 504a and 504b for receiving cartridge 501. (Tamper-evident cap 200 may not normally be visible when cartridge 501 is disengaged from vibratory cradle 503. In FIG. 5, cartridge 501 is configured as it would be when fully inserted into vibratory cradle 503, as is explained in more detail below.) Vibratory cradle 503 is configured to hold cartridge at an angle Θ from horizontal. In this example, angle Θ is 10 degrees, but other angles may be used, so long as tamper-evident caps stored in cartridge 501 will remain stationary when cartridge 501 is not vibrated, but will feed toward outlet 502 when cartridge 501 is vibrated.

Cartridge 501 may also comprise a hook feature 505, for removably retaining cartridge in finishing station 300. For example, finishing station 300 may include a "push push" mechanism of the type available from Southco, Inc. of Concordville, Pennsylvania, USA. A "push push" mechanism is one that latches cartridge 501 into finishing station 300 when cartridge 501 is simply pushed into finishing station 300, and then releases cartridge 501 in response to a subsequent push of cartridge 501 toward finishing station 300. In other embodiments, cartridge 501 may be removably retained in finishing station 300 using any other workable kind of mechanism, for example a motor-driven latch.

Figure 6:
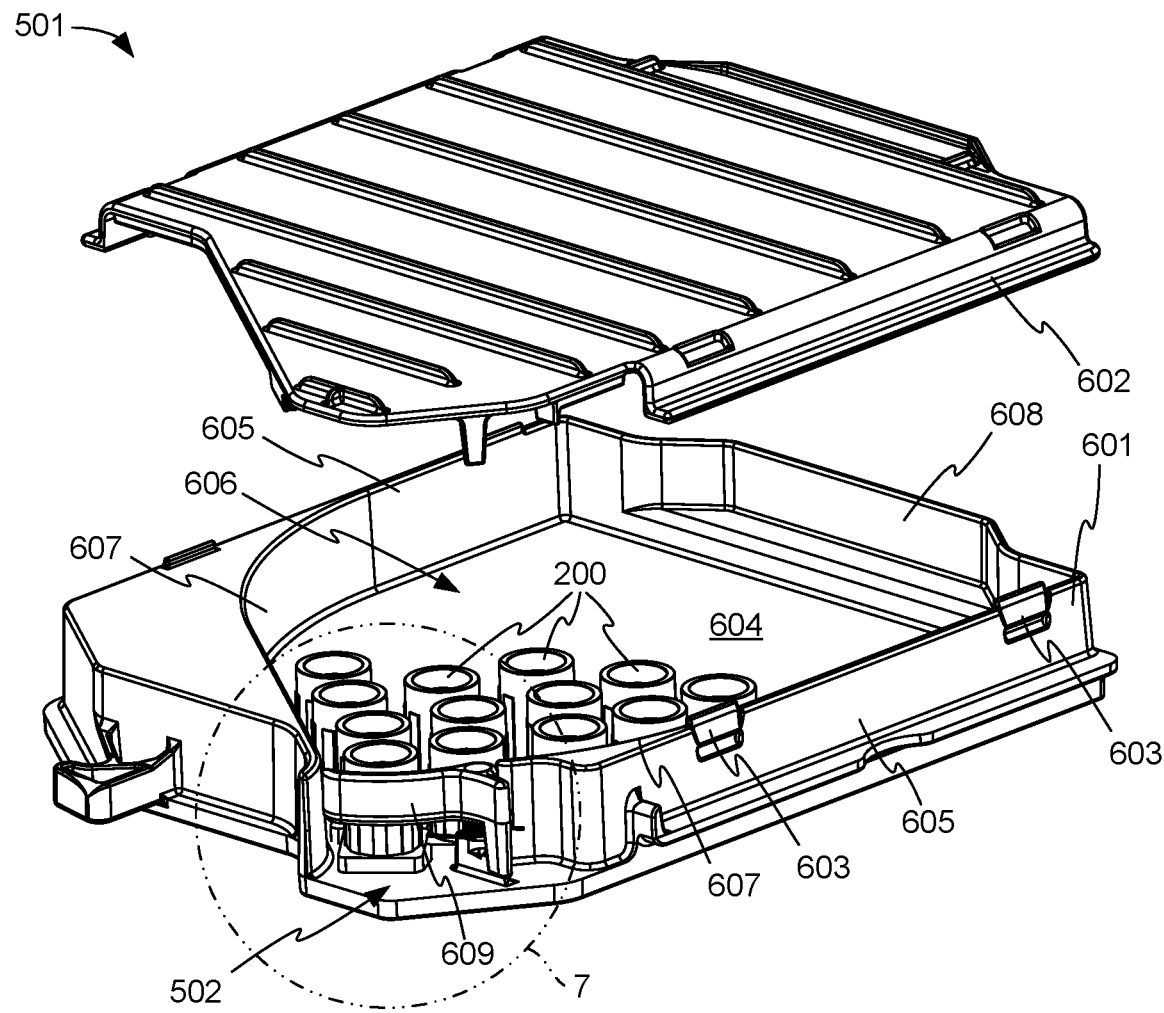
FIG. 6 shows a partially-exploded view of a cartridge, partially filled with tamper-evident caps, in accordance with embodiments of the invention.

FIG. 6 shows a partially-exploded view of cartridge 501, partially filled with tamper-evident caps 200, in accordance with embodiments of the invention. Cartridge 501 may have a clamshell design, including a lower portion 601 and a lid 602. Lid 602 can preferably snap onto lower portion 601 using snap features 603, and can preferably be removed from lower portion 601 without the use of tools.

Cartridge 501 includes a floor 604 and side walls 605 rising from opposite edges of the floor. The floor and side walls define a storage volume 606 for holding the tamper-resistant caps 200. Side walls 605 include curved sections 607 that approach each other such that storage volume 606 narrows toward outlet 502 of cartridge 501. Cartridge 501 further includes an end wall 608 opposite outlet 502.

Figure 7:
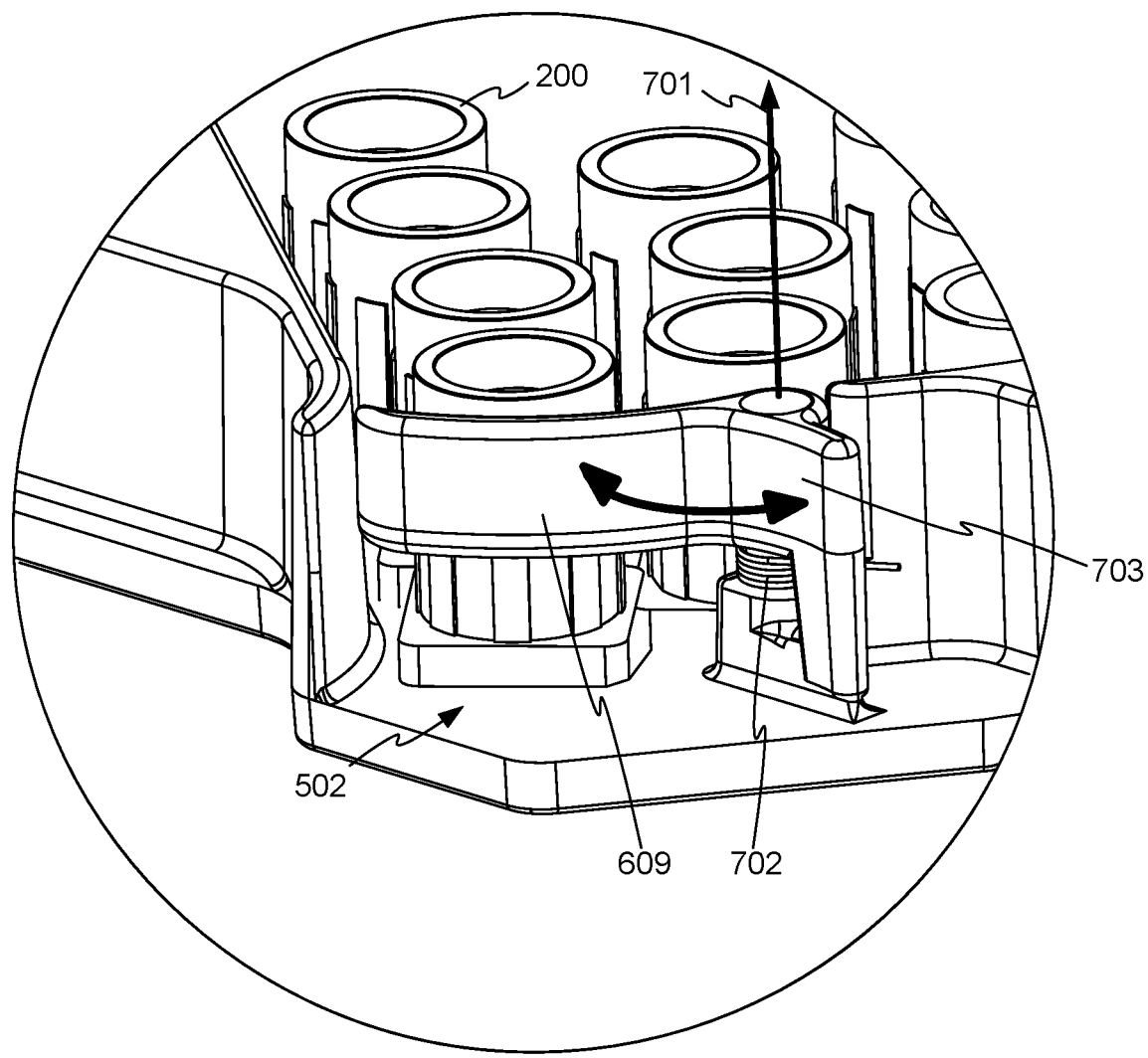
FIG. 7 shows a door of the cartridge of FIG. 6.

Cartridge 501 includes a spring-loaded door 609 at outlet 502. FIG. 7 shows door 609 in more detail. Door 609 is configured to rotate about axis 701, but by default, when cartridge 501 is not inserted into the robotic compounding device, door 609 is held in the illustrated "closed" configuration by torsion spring 702. Torsion spring 702 is strong enough to hold the supply of tamper-evident caps 200 in cartridge 501. A lever 703 is provided on door 609 for opening door 609 when cartridge 501 is inserted into the robotic compounding device, as is explained in more detail below.

Figure 8:
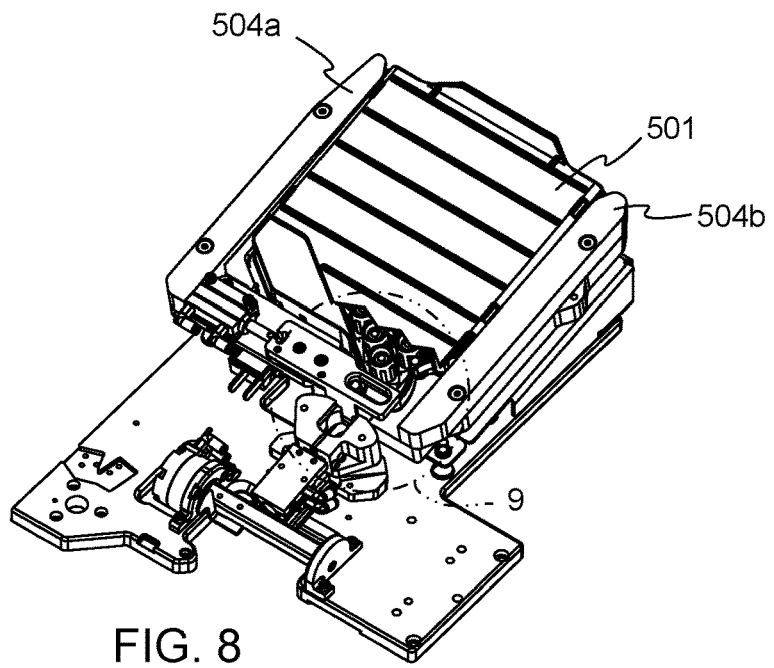
FIG. 8 shows a partially-cutaway view of the cartridge of FIG. 6, after it has been inserted into rails of the finishing station of FIG. 3, in accordance with embodiments of the invention.
Figure 9:
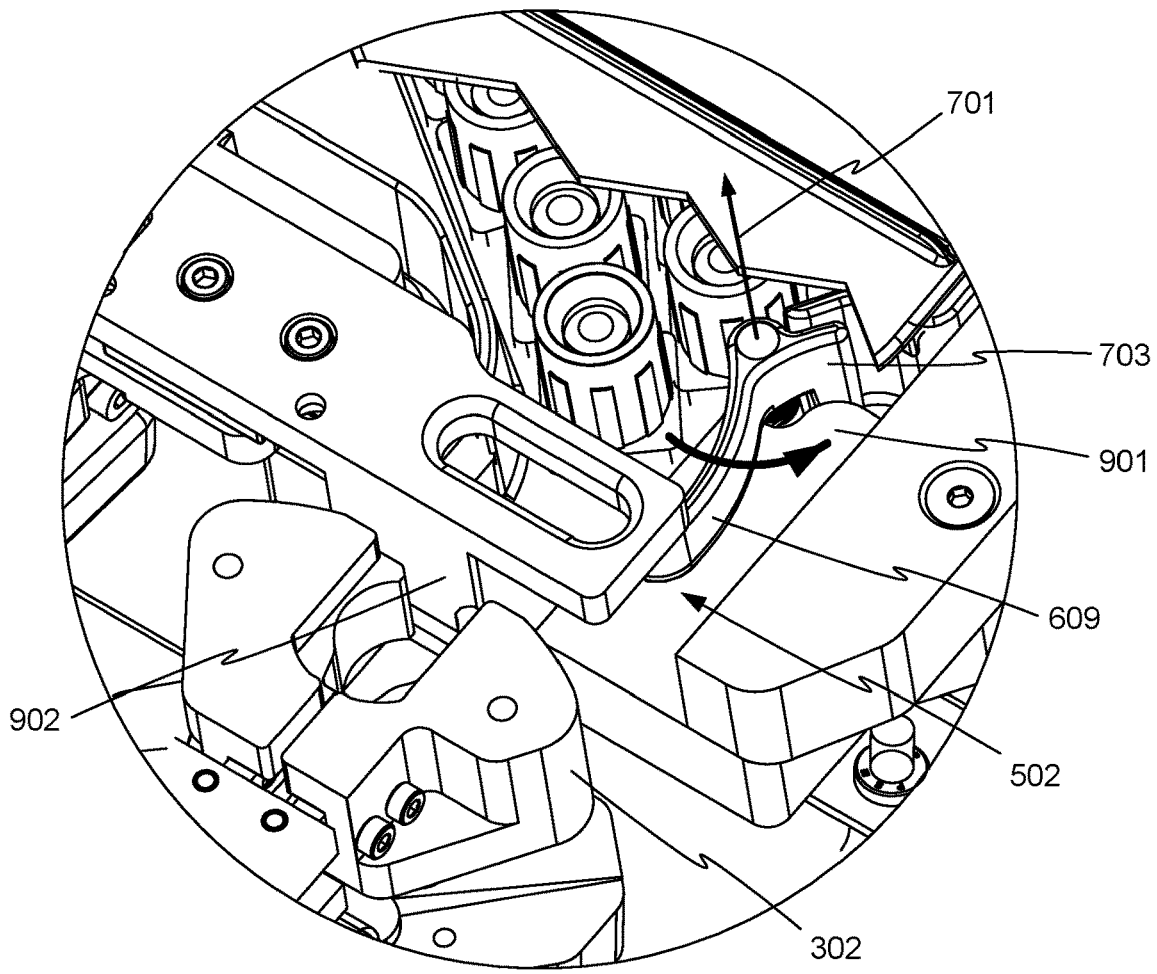
FIG. 9 shows a portion of FIG. 8 in more detail.

FIG. 8 shows a partially-cutaway view of cartridge 501 after it has been inserted into channels 504a and 504b. FIG. 9 shows a portion of FIG. 8 in more detail. As is visible in FIG. 9, door 609 of cartridge 501 is swung open about axis 701 as lever 703 encounters a finger 901 of syringe finishing station 300. With door 609 open, tamper-evident caps 200 can flow out of outlet 502, once vibration starts.

If cartridge 501 is removed from syringe finishing station 300 while still holding tamper-evident caps, spring 702 is preferably strong enough to close door 609, pushing any partially-dispensed tamper-evident caps 200 back into cartridge 501. Cartridge 501 may thus be "hot swappable", meaning that it can be removed and re-inserted or replaced with another cartridge at any time.

A gate 902 may be present just beyond outlet 502. In FIG. 9, gate 902 is shown in a closed position, so while tamper-evident caps 200 can leave cartridge 501, they still will not reach gripper 302 so long as gate 902 is closed.

Figure 10:
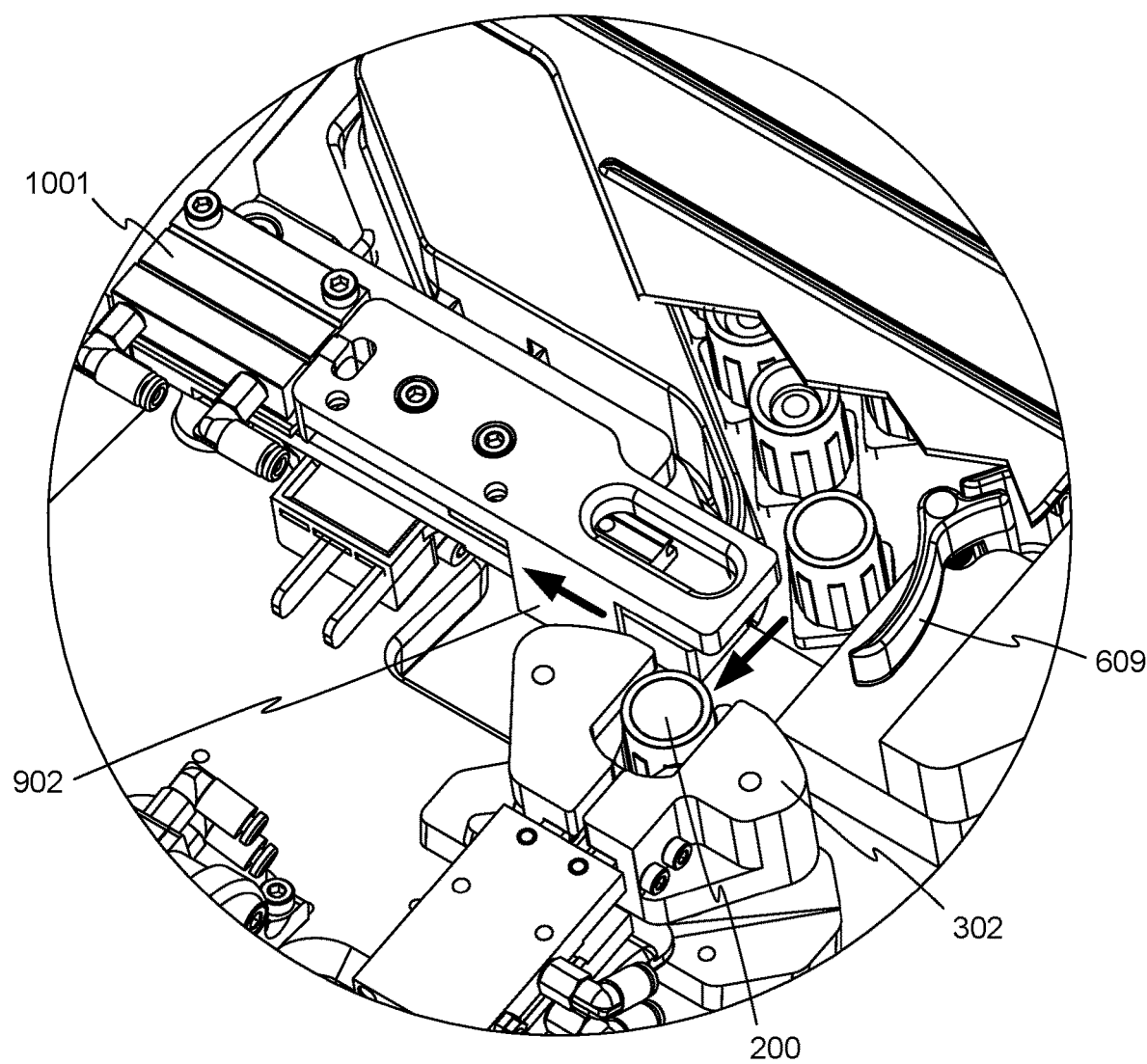
FIG. 10 shows a similar view as FIG. 9, with a gate open.

FIG. 10 shows a similar view as FIG. 9, with gate 902 open. Gate 902 may be actuated by any suitable actuator, for example a pneumatic actuator 1001. With both door 609 and gate 902 open, a tamper-evident cap 200 can slide (due to gravity and vibration) into gripper 302. Gripper 302 may then place tamper-evident cap 200 on a syringe, as described above. Preferably, gate 902 is opened only when it is desired to dispense a tamper-evident cap 200 into gripper 302. Once a cap 200 is dispensed, gate 902 may be closed. In addition, cartridge 501 is also preferably vibrated only when it is desired to dispense a tamper evident cap 200 into gripper 302.

Figure 11:
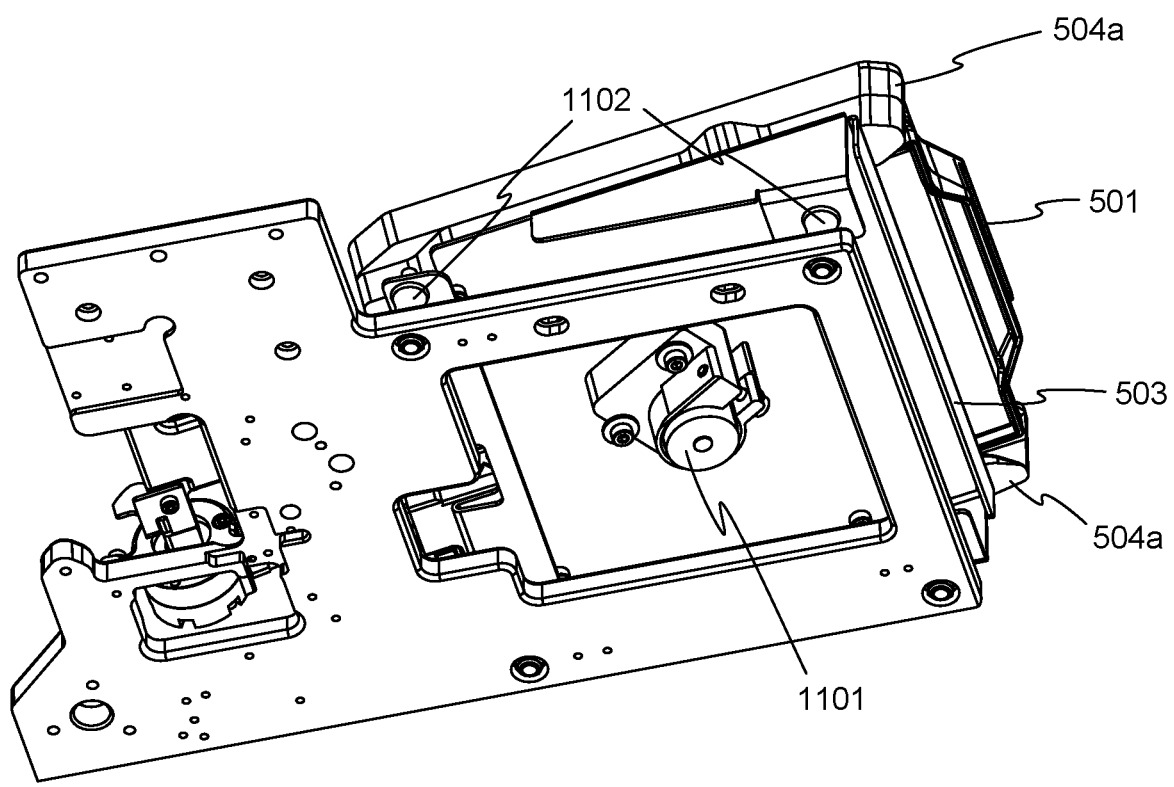
FIG. 11 shows a lower oblique view of vibratory cradle, in accordance with embodiments of the invention.

Vibration of cartridge 501 may be accomplished in any workable manner. FIG. 11 shows a lower oblique view of vibratory cradle 503, holding cartridge 501 between channels 504a and 504b. A vibratory mechanism 1101 is mounted to the bottom of vibratory cradle 503, and can impart vibration to vibratory cradle 503 and cartridge 501. Vibratory mechanism 1101 may be, for example, a motor with an eccentric weight attached, a voice coil, a piezoelectric element, or another kind of vibratory mechanism. A controller of the robotic compounding device can control vibratory mechanism 1101 to vibrate when desired, for example during dispensing of a tamper-evident cap 200 from cartridge 501 to gripper 302.

Vibratory cradle 503 may be mounted on flexible grommets or mounts 1102, to attenuate the amount of vibration transmitted to syringe finishing station 300 and other parts of the robotic compounding device.

FIG. 12 illustrates a tool 1200 for efficient filling of cartridge 501 with tamper-evident caps 200, in accordance with embodiments of the invention. Tool 1200 includes a main body 1201 that has two side portions 1202 and 1203, joined by a hinge 1204. Conveniently, main body 1201 is a single, monolithic body, and hinge 1204 is a living hinge. For example, main body 1201 may be molded from a polymer, and hinge 1204 formed by a thinned area of main body 1201. In other embodiments, separate pieces may be attached to parts of a separate hinge.

Two rows of gripping features 1205 descend from the main body 1201, one row of gripping features 1205 on each side of hinge 1204. Two rows of openings 1206 are provided, corresponding gripping features 1205. Openings 1206 may facilitate the flow of first air to tamper-evident caps held in tool 1200 during use.

Two levers 1207*a* and 1207*b* are attached respectively to outer edges of main body 1201. Each lever has a proximal end 1208, attached to main body 1201, and a distal end 1209. Distal ends 1209 may conveniently have loops as shown, for easy operation by hand. Levers 1207*a* and 1207*b* may conveniently be identical parts snapped onto main body 1201, but other arrangements are possible. For example, levers 1207*a* and 1207*b* need not be identical, may be attached to main body 1201 with fasteners, may be formed integrally with main body 1201, or may be formed or attached in any other workable manner. Levers 1207*a* and 1207*b* are crossed, but need not be connected to each other by an axle or pivot.

As shown in FIG. 13 and FIG. 14, gripping features 1205 may be spaced to correspond to a package 1301 of tamper-evident caps 200, as may be supplied by a manufacturer of tamper-evident caps 200. FIG. 13 shows tool 1200 poised to engage with package 1301 of tamper-evident caps 200, and FIG. 14 is a cross section view of tool 1200 and package 1301 after engagement.

Figure 15:
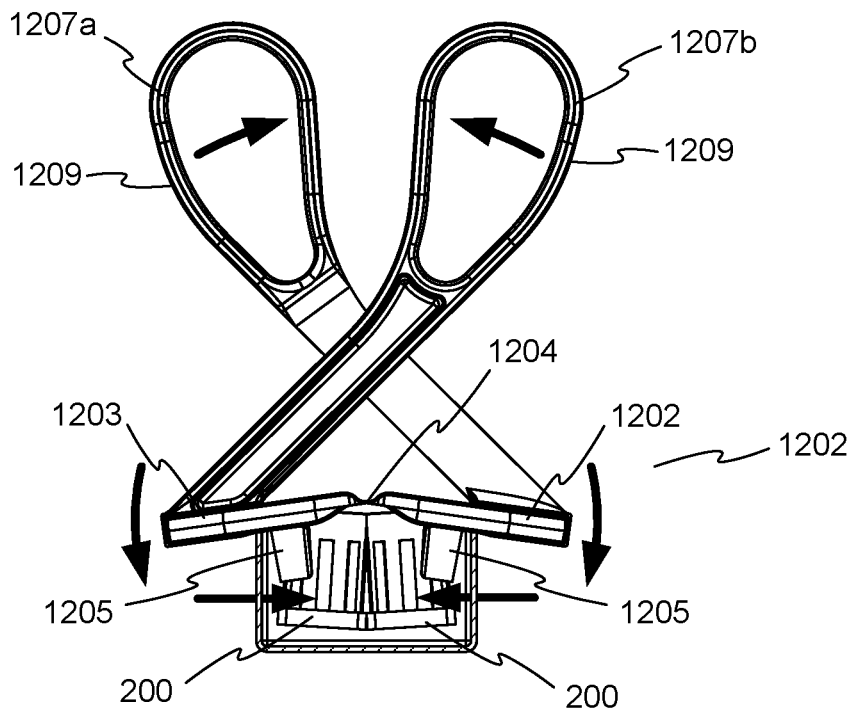
FIG. 15 shows a stage in the operation of the tool of FIG. 12, in accordance with embodiments of the invention.

As shown in FIG. 15, when distal ends 1209 of levers 1207*a* and 1207*b* are brought closer together, the two side portions 1202 and 1203 of main body 1201 flex about hinge 1204. This brings the rows of gripping features 1205 toward each other, clamping tamper-evident caps 200 between them.

Figure 16:
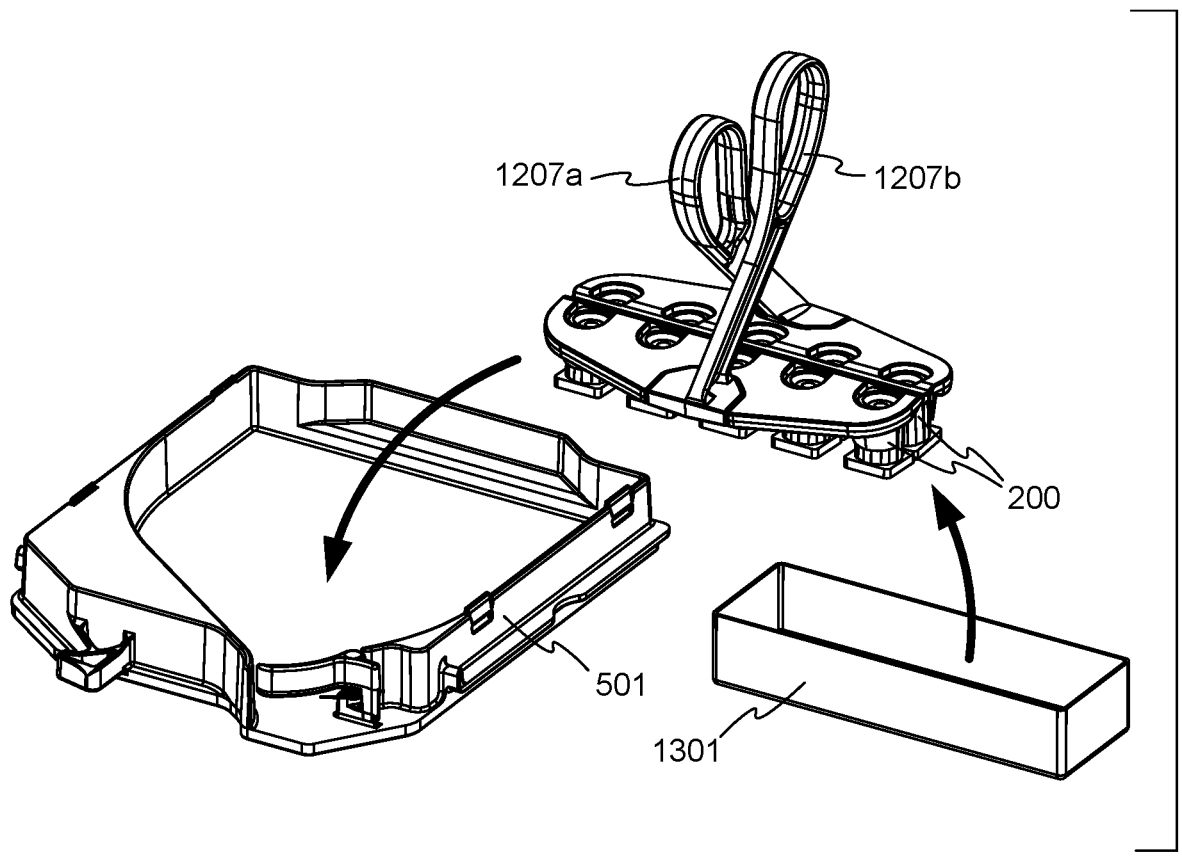
FIG. 16 shows another stage in the operation of the tool of FIG. 12, in accordance with embodiments of the invention.
Figure 17:
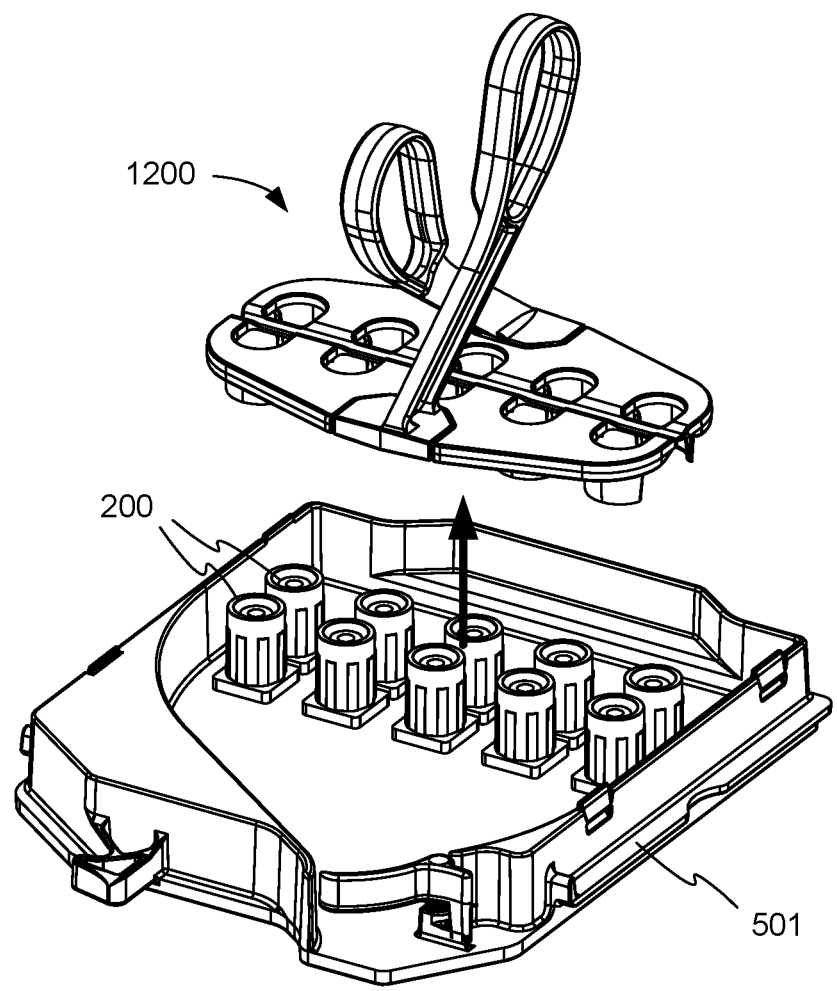
FIG. 17 shows another stage in the operation of the tool of FIG. 12, in accordance with embodiments of the invention.

As shown in FIG. 16, while pressure is maintained on levers 1207*a* and 1207*b*, tool 1200 and tamper-evident caps 200 can be lifted out of package and conveniently transferred to cartridge 501 (shown without lid 602). FIG. 17 shows a later stage in the transfer. Tamper-evident caps 200 have been deposited in cartridge 501. Tool 1200 has been allowed to release tamper-evident caps 200, and has been lifted away from cartridge 501.

This technique enables filling of cartridge 501 much more efficiently than moving tamper-evident caps 200 into cartridge 501 one at a time manually.

It is to be understood that all workable combinations of the features disclosed herein are also considered to be disclosed.

The invention has now been described in detail for purposes of clarity and understanding. However, it will be appreciated that certain changes and modifications may be practiced within the scope of the appended claims.

What is claimed is:

1. A method of loading tamper-evident syringe caps into a robotic compounding device, the method comprising:
    providing a cartridge having a storage volume for containing the tamper-evident syringe caps, wherein the cartridge comprises:
        a flat floor;
        opposing side walls rising from the floor, the floor and side walls defining the storage volume, and the side walls including curved sections that approach each other such that the storage volume narrows toward an outlet of the cartridge;
        an end wall opposite the outlet of the cartridge;
        a cover that snaps onto the side walls to enclose the storage volume; and
        a spring-loaded door that by default closes off the outlet of the cartridge;
    placing a supply of tamper-evident syringe caps into the cartridge; and
    inserting the cartridge into the robotic compounding device.

2. The method of claim 1, wherein the robotic compounding device comprises a syringe finishing station.

3. The method of claim 2, wherein the syringe finishing station comprises:
    an input location configured to individually receive tamper-evident caps from the cartridge; and
    a gate at the input location, and the method further comprising opening the gate to selectively admit one of the tamper-evident caps from the outlet of the cartridge.

4. The method of claim 3, the robotic compounding device further comprising a capping mechanism configured to attach a tamper-evident cap to a syringe.

5. The method of claim 4, wherein the capping mechanism comprises a gripper and a pneumatic actuator.

6. The method of claim 5, wherein the input location comprises the gripper of the capping mechanism.

7. The method of claim 6, further comprising:
    positioning the gripper adjacent to the gate;
    opening the gate and the door; and
    dispensing one tamper-evident cap into the gripper.

8. The method of claim 7, further comprising closing the gate and the door after the one tamper-evident cap is dispensed into the gripper.

9. The method of claim 8, wherein the cartridge is vibrating during dispensing of the one tamper-evident cap into the gripper.

10. The method of claim 3, wherein the gate is opened via a pneumatic actuator.

11. The method of claim 1, the cartridge further comprising a hook adjacent the outlet, for removably retaining the cartridge in a compounding system.

12. The method of claim 11, wherein inserting the cartridge into the robotic compounding device latches the cartridge into the robotic compounding device via the hook.

13. The method of claim 1, further comprising opening the spring-loaded door with the robotic compounding device.

14. The method of claim 13, wherein the spring-loaded door comprises a lever extending outward from the spring-loaded door, and wherein opening the spring-loaded door comprises manipulating the lever to open the spring-loaded door.

15. The method of claim 1, further comprising vibrating the cartridge to cause tamper-evident caps to travel under the influence of gravity toward an outlet of the cartridge.

16. The method of claim 1, wherein the cover can be disengaged from the rest of the cartridge without the use of tools.

17. The method of claim 1, wherein the cartridge comprises a clamshell design.

18. The method of claim 1, wherein the spring of the spring-loaded door comprises a torsion spring.

* * * * *